United States Patent
Sherman et al.

(10) Patent No.: US 10,426,705 B2
(45) Date of Patent: Oct. 1, 2019

(54) COLOSTRUM COLLECTION SYSTEM

(71) Applicant: LANSINOH LABORATORIES, INC., Alexandria, VA (US)

(72) Inventors: Jules P. Sherman, Palo Alto, CA (US); Rush Lloyd Bartlett, II, Mountain View, CA (US); Frank T. Wang, Cupertino, CA (US); Ryan J. F. Van Wert, Palo Alto, CA (US)

(73) Assignee: LANSINOH LABORATORIES, INC., Alexandria, VA (US)

( * ) Notice: Subject to any disclaimer, the term of this patent is extended or adjusted under 35 U.S.C. 154(b) by 278 days.

(21) Appl. No.: 15/380,155

(22) Filed: Dec. 15, 2016

(65) Prior Publication Data

US 2017/0095600 A1    Apr. 6, 2017

Related U.S. Application Data

(63) Continuation-in-part of application No. 14/611,693, filed on Feb. 2, 2015, now Pat. No. 10,080,825, which
(Continued)

(51) Int. Cl.
*A61J 7/00* (2006.01)
*A61M 39/10* (2006.01)
(Continued)

(52) U.S. Cl.
CPC ............ *A61J 7/0053* (2013.01); *A61M 1/062* (2014.02); *A61M 39/105* (2013.01);
(Continued)

(58) Field of Classification Search
None
See application file for complete search history.

(56) References Cited

U.S. PATENT DOCUMENTS 3,911,920 A    10/1975   Susinn
4,263,912 A *   4/1981   Adams ................ A61M 1/06
                                                      604/523
(Continued)

FOREIGN PATENT DOCUMENTS

| EP | 0000339 | 1/1979 |
| JP | 2003-299727 | 10/2003 |
| WO | 2014143130 | 9/2014 |

OTHER PUBLICATIONS

International Search Report and Written Opinion in PCT/US2017/065736, dated Mar. 21, 2018, 11 pages.
(Continued)

*Primary Examiner* — Bhisma Mehta
*Assistant Examiner* — Matthew A Engel
(74) *Attorney, Agent, or Firm* — Merchant & Gould P.C.

(57) ABSTRACT

An adapter system for facilitating collection of colostrum from a breast may include an adapter, a removable reservoir and a hand-expression funnel. The adapter may include a first open end for connecting to a breast shield of a breast pump system, a second open end for connecting to a breast pump connector of the breast pump system, and a third open end, disposed between the first and second open ends. The removable reservoir may include a wide end for removably attaching to the third open end and a narrow end for attaching to a colostrum delivery device. The hand-expression funnel may include a wide end for receiving colostrum and a narrow end for attaching to the colostrum delivery device. In some embodiments, the colostrum delivery device is a syringe.

10 Claims, 14 Drawing Sheets

Related U.S. Application Data is a continuation-in-part of application No. 14/478,713, filed on Sep. 5, 2014, now Pat. No. 10,086,120.

(60) Provisional application No. 61/899,482, filed on Nov. 4, 2013, provisional application No. 61/874,303, filed on Sep. 5, 2013.

(51) Int. Cl.
*A61M 39/22* (2006.01)
*A61M 1/06* (2006.01)

(52) U.S. Cl.
CPC ..... *A61M 39/22* (2013.01); *A61M 2039/1033* (2013.01); *A61M 2039/1077* (2013.01); *A61M 2205/3379* (2013.01)

(56) References Cited

U.S. PATENT DOCUMENTS

| | | | |
|---|---|---|---|
| 4,323,067 A * | 4/1982 | Adams | A61K 49/0004 435/7.23 |
| 4,799,922 A * | 1/1989 | Beer | A61M 1/06 119/14.49 |
| 4,856,663 A | 8/1989 | Epp | |
| 4,857,051 A * | 8/1989 | Larsson | A61M 1/06 604/74 |
| 4,884,013 A | 11/1989 | Jackson | |
| 4,930,652 A | 6/1990 | Murphy | |
| 4,961,726 A * | 10/1990 | Richter | A61M 1/0037 604/313 |
| 4,964,851 A * | 10/1990 | Larsson | A61M 1/0023 604/248 |
| 4,966,580 A | 10/1990 | Turner | |
| 5,531,338 A * | 7/1996 | Sklar | A61J 9/00 215/11.1 |
| 5,542,921 A * | 8/1996 | Meyers | A61M 1/06 604/315 |
| 5,728,137 A | 3/1998 | Anderson | |
| 5,810,772 A * | 9/1998 | Niederberger | A61M 1/06 604/346 |
| 5,941,847 A * | 8/1999 | Huber | A61M 1/066 604/74 |
| 5,957,081 A | 9/1999 | Van Der Lely | |
| RE36,324 E | 10/1999 | Yoda | |
| 6,023,639 A | 2/2000 | Hakky | |
| 6,110,140 A * | 8/2000 | Silver | A61M 1/06 604/118 |
| 6,200,295 B1 | 3/2001 | Burchett | |
| 6,461,324 B1 * | 10/2002 | Schlensog | A61M 1/06 604/74 |
| 6,471,660 B1 * | 10/2002 | Covington | A61K 49/0004 435/7.23 |
| 6,497,677 B2 * | 12/2002 | Silver | A61M 1/06 604/74 |
| 6,884,229 B2 | 4/2005 | Renz | |
| 6,966,904 B2 | 11/2005 | Ruth | |
| 7,029,454 B2 * | 4/2006 | Watanabe | A61M 1/06 604/74 |
| 7,048,120 B2 | 5/2006 | Pond | |
| 7,320,678 B2 | 1/2008 | Ruth | |
| 7,413,557 B2 * | 8/2008 | Samson | A61M 1/06 604/74 |
| 7,648,467 B2 | 1/2010 | Wang | |
| 7,662,127 B2 * | 2/2010 | Silver | A61M 1/064 604/74 |
| 7,875,000 B2 * | 1/2011 | Krebs | A61M 1/06 604/523 |
| 8,052,635 B1 * | 11/2011 | Kelly | A61M 1/0037 604/74 |
| 8,360,102 B2 | 1/2013 | Khouri | |
| 8,979,819 B2 | 3/2015 | Sherman | |
| 8,998,879 B2 | 4/2015 | Sherman | |
| 9,248,077 B1 | 2/2016 | Kelly | |
| 9,623,160 B2 * | 4/2017 | Alvarez | A61M 1/062 |
| 9,642,952 B1 * | 5/2017 | Kelly | A61M 1/0066 |
| 9,782,526 B2 * | 10/2017 | Sherman | A61M 1/068 |
| 10,080,825 B2 | 9/2018 | Bartlett | |
| 10,086,120 B2 | 10/2018 | Bartlett | |
| 2002/0072701 A1 * | 6/2002 | Nuesch | A61M 1/06 604/74 |
| 2002/0156419 A1 | 10/2002 | Silver | |
| 2004/0178162 A1 | 9/2004 | Zucker-Franklin | |
| 2006/0025718 A1 * | 2/2006 | Ostrowski | A61J 9/00 604/74 |
| 2007/0118078 A1 | 5/2007 | McNally | |
| 2007/1011807 | 5/2007 | McNally | |
| 2007/0235405 A1 | 10/2007 | Fatema | |
| 2008/0021380 A1 * | 1/2008 | Thommen | A61M 1/06 604/74 |
| 2008/0039778 A1 | 2/2008 | Goldie | |
| 2008/0255503 A1 * | 10/2008 | Quackenbush | A61M 1/0031 604/74 |
| 2009/0227943 A1 | 9/2009 | Schultz | |
| 2009/0254028 A1 | 10/2009 | Brittner | |
| 2010/0049122 A1 | 2/2010 | Jaeger-Waldau | |
| 2010/0324477 A1 * | 12/2010 | Paterson | A61M 1/06 604/74 |
| 2011/0054436 A1 | 3/2011 | Griffis | |
| 2011/0168292 A1 | 7/2011 | Luzbetak | |
| 2011/0251552 A1 | 10/2011 | Brittner | |
| 2012/0232524 A1 | 9/2012 | Hyun | |
| 2012/0265169 A1 * | 10/2012 | Sherman | A61M 1/06 604/514 |
| 2013/0005023 A1 | 1/2013 | Min | |
| 2013/0030379 A1 | 1/2013 | Ingram | |
| 2013/0281983 A1 * | 10/2013 | Sherman | A61M 1/06 604/514 |
| 2014/0052106 A1 * | 2/2014 | Sherman | A61J 9/00 604/514 |
| 2014/0135683 A1 | 5/2014 | Hradisky | |
| 2014/0180205 A1 * | 6/2014 | Lee | A61M 1/0023 604/74 |
| 2014/0276629 A1 * | 9/2014 | Bauer | A61M 1/06 604/514 |
| 2014/0288466 A1 * | 9/2014 | Alvarez | A61M 1/06 601/6 |
| 2015/0065996 A1 * | 3/2015 | Bartlett, II | A61M 1/062 604/514 |
| 2015/0133894 A1 * | 5/2015 | Sherman | A61J 9/00 604/514 |
| 2015/0148783 A1 * | 5/2015 | Bartlett, II | A61M 1/062 604/514 |
| 2015/0196696 A1 | 7/2015 | Sherman | |
| 2015/0283311 A1 * | 10/2015 | Alvarez | A61M 1/0031 604/514 |
| 2016/0331879 A1 | 11/2016 | Dann | |
| 2017/0095600 A1 * | 4/2017 | Sherman | A61M 39/105 |

OTHER PUBLICATIONS

International Search Report and Written Opinion in PCT/US2014/054377, dated Dec. 22, 2014, 7 pages.
International Search Report and Written Opinion in PCT/US2013/050464, dated Oct. 24, 2013, 12 pages.
International Search Report and Written Opinion in PCT/US2013/051142, dated Oct. 22, 2013, 11 pages.

\* cited by examiner

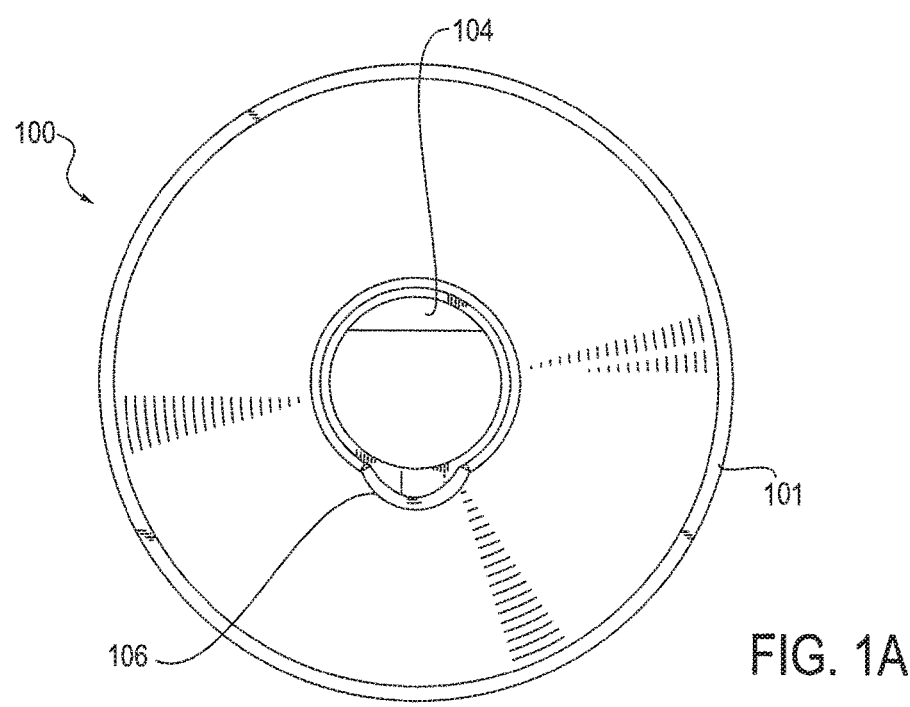
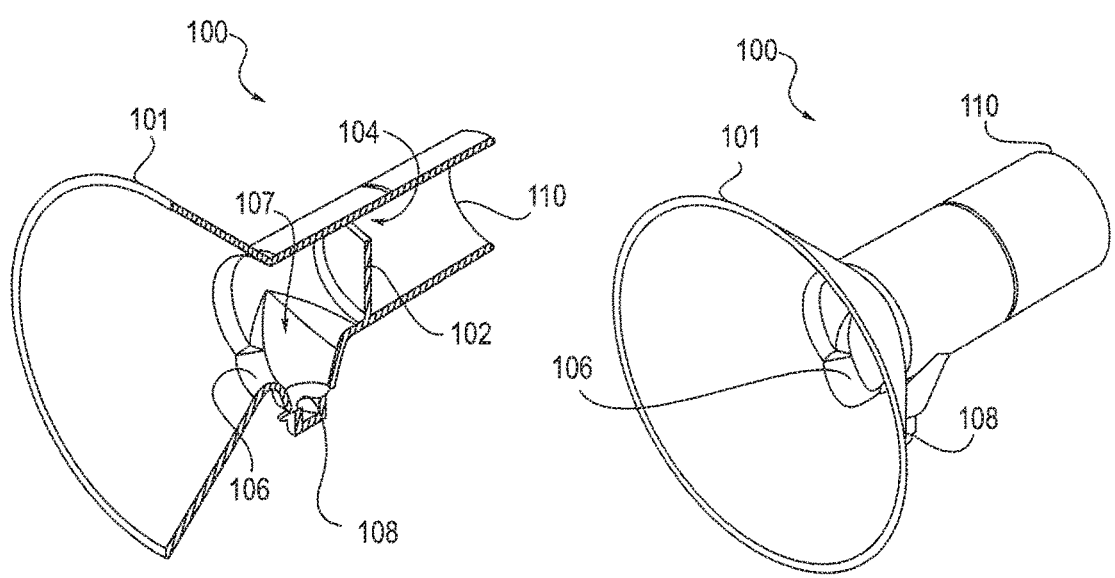
FIG. 1A
FIG. 1B
FIG. 1C

COLOSTRUM COLLECTION SYSTEM

CROSS-REFERENCE TO RELATED APPLICATIONS

This application is a continuation-in-part of U.S. patent application Ser. No. 14/611,693, entitled "Connector for Collection and Dispensing of Breast Milk or Colostrum," filed Feb. 2, 2015, now U.S. Pat. No. 10,080,825, which is a continuation-in-part of U.S. patent application Ser. No. 14/478,713, entitled "Connector for Collection and Dispensing of Breast Milk or Colostrum," filed Sep. 5, 2014, now U.S. Pat. No. 10,086,120, which claims benefit of U.S. Provisional Patent Application Ser. Nos. 61/874,303, filed on Sep. 5, 2013; and 61/899,482, filed on Nov. 4, 2013. The disclosures of the above referenced patent applications are hereby fully incorporated by reference.

BACKGROUND

Colostrum is the first nutritional liquid that comes out of the breast during lactation and is a very important food substance for development of a healthy newborn. This highly nutritional material is also packed with antibodies and other immune enhancing substances. Colostrum is produced at a very slow rate—a few milliliters per hour—and generally requires some form of pumping and/or hand expression to express it from the breast. Additionally, breast milk sometimes is expressed in small volumes, especially towards the beginning and end of the expression time. Thus, although colostrum is critical for early newborn nutrition, it is only produced in very small quantities and can be difficult to collect.

Currently, colostrum is typically collected using a funnel, also called a breast flange or shield, which connects to a large collection container (such as a milk bottle), typically via a one way valve. Alternatively, hand expression is performed on the breast, and colostrum is collected in a spoon, small cup, or small vial. These collection containers (bottle, spoon, etc.) require transfer to another container—typically a small syringe—for administering small volumes of colostrum to the newborn. This transfer of material from collection container to administration container leads to at least some amount of wasted colostrum, despite the fact that the total collected amount is very small to begin with. The inherent difficulty in collecting and administering colostrum leads many nursing mothers to become discouraged and not collect any colostrum at all. This difficulty also sometimes leads to mothers giving up on breast feeding altogether.

Therefore, it would be advantageous to have improved devices, systems and methods for collecting and administering colostrum. Ideally, such devices, systems and methods would also be applicable for collecting and administering breast milk. Also ideally, such devices, systems and methods would be relatively easy to use and would eliminate the step of transferring colostrum and/or breast milk from a collection container to an administration device. The embodiments described below address at least some of these objectives.

BRIEF SUMMARY

The disclosure herein describes an adapter, a system, and a method for collecting colostrum and/or breast milk from a breast of a female human or animal. In some embodiments, the adapter, system and/or method may be used for both collection and administration of colostrum and/or breast milk. Many of the embodiments and features described in this application are designed specifically for collection and delivery of colostrum, and thus many of the descriptions below focus on that use. However, many, if not all, of these embodiments and features may also be used for collection and delivery of breast milk. Although the below description will not always repeat the statement that the various embodiments may be used for colostrum, breast milk or both, the scope of the invention covers any and all such uses.

In general, the adapter is compatible with a funnel, breast flange/shield, and/or funnel with a flange or connector, such that the connector can facilitate capture and dispensing of breast milk and/or colostrum from a syringe or other compatible collection/administration device. The container, catchment device(s), valves, and connectors may optionally be lubricated, to facilitate the movement of breast fluids, such as colostrum and/or breast milk, into a catchment area. The catchment area collects the fluid and allows it to easily be drawn into, or flow into, a syringe via a connector.

The connector may attach to the front or the rear of a cylindrical syringe with a plunger for expelling material post-capture and/or a plunger for moving to suck or pull material into the barrel of the syringe during capture. The container that is coupled with the adapter to collect colostrum and/or milk does not have to be a syringe, but may alternatively be any container that can connect via a connection means to the funnel adapter and then expel the material from the same container. This may include, but is not limited to, an attached bag, a vacuutainer, a bottle, a rectangular or odd shaped catchment container, a compressible container, a rollable container, or any other container that can connect to a capture funnel or comprise a capture funnel that also may serve to deliver the material to the infant. A "container" may also be referred to herein as a "fluid collection device," which has a synonymous meaning for the purposes of this application. Thus, a fluid collection device may be any of the types of containers listed above or any other suitable container for use with the adapter and/or system described herein for collection of colostrum and/or milk.

Lubricant or frictional material on the surface of the connectors may serve to facilitate connection to the syringe and or the funnel section or they may serve to allow for rapid flow with less adhesion of the breast product on the wall of the container. This lubricant or frictional material may or may not increase or decrease friction as desired in different regions. Additionally, it may be pressure sensitive through shear thickening or shear thinning. It may be silicone, nano-printed with interspaced fluid, or other lubricious or frictionous coating. To increase friction, a sand or imprinted/dimpled area may be used, if desired in connector regions.

The connector for the syringe or other container to the funnel and/or an adapter that fits both a funnel and a container, may comprise a Luer connector, press fit connector, tapered section, screw thread, tube attachment, or other means of attaching a syringe or other container with an adapter or funnel that may serve to capture and dispense colostrum.

The funnel and/or adapter to a funnel may also comprise a catchment reservoir to accumulate droplets of material to or near the connector. The catchment reservoir and surrounding area may optionally be coated with a lubricious material to facilitate movement of material or cause less adhesion to the wall. The catchment area guides the flow of material to the connector when the adapter or the funnel is in the appropriate configuration. Additionally, a block or guide may serve to facilitate flow into the catchment reservoir, while also including an opening to create a suction force. This opening may be in any area of the block, but one ideal location may in the top half of the block, away from the catchment reservoir side.

Additionally, an adapter or a funnel may also comprise a system that has two catchment containers of different sizes. In one such example the front container comprising a syringe may be smaller than a back container comprising a bottle or catchment jar. The syringe in the front container may serve to extract small volumes of material where the catchment jar in the back may serve to capture large volumes of materials. The small volume container may be arranged such that it can catch material stopped by a block, while the large container would be filled via the hole in the block that allows for flow into the larger container. There may or may not be a one way valve that helps prevent reverse flow from the larger container and/or flow into the vacuum port in the attachment area of the larger container. This vacuum port in the larger container also comprises vacuum through the hole in the block that is used as a flow-through area to fill the larger container or not used as a flow-through area when the smaller container is desired to be filled. The funnel may be rotated, or a rotational mechanism within the adapter may be used, if it is desired to keep the funnel stationary if the user wants to switch from extracting small volumes with the syringe to large volumes with the large container. Additionally, the large container could also include attachment means for a syringe or suction port to be used in the catchment area of the funnel or the adapter.

Also disclosed is a method for capture and dispensing of colostrum or other milk product. A funnel with a connector to a small container or an adapter to an existing funnel with a connector is used to capture and dispense milk product to an infant. The mechanism of capture is through a funnel, which allows milk product to flow into a catchment area or catchment reservoir. This catchment area or reservoir may or may not be formed by a depression in the side or by the function of a block in the internal section of the opening of the funnel that, when placed on a side orientation, forms a catchment area to collect fluid or viscous material. The block may also have an opening opposite the catchment area, such that air flow or vacuum may facilitate the movement of material out of a breast/nipple. The catchment of the material also comprises a connector that is attachable to a delivery device such as but not limited to a syringe. This delivery device may actively suck up material from the catchment area or may have an opening large enough such that flow from the catchment area into the delivery device can be accomplished with air venting out one or more openings, not excluding the opening forming the connection with the catchment area. The delivery device, once containing captured material, is used to deliver milk product after detachment from the adapter or funnel with the connector. After detachment, the delivery device is used with a feeding tube or without a feeding tube to administer the milk or colostrum material to the infant or newborn of any species, including but not limited to humans, horses, dogs, cats, hamsters, whales, or any other type of mammal.

In one aspect of the present disclosure, an adapter for use in a system for collecting colostrum and/or milk from a breast may include: a body having a predominantly cylindrical shape; a first open end of the body for connecting to a funnel device; a second open end of the body for connecting to a source of suction; a side port between the first and second ends for connecting to a fluid collection device; a catchment area at or near the side port; and a blocking member between the side port and the second end, for preventing colostrum from passing beyond the side port and through the second end. The blocking member may include at least one aperture for allowing suction force to be transmitted from the second end to the first end.

In some embodiments, the side port is configured to connect to a syringe. In other embodiments, the side port is configured to connect to a tube that connects to a syringe. I still other embodiments, the side port is configured to connect to any other suitable collection device. In some embodiments, the adapter is configured to attach to a breast pump system. In some embodiments, the catchment area comprises a depression in the body adjacent the side port. In one embodiment, for example, the catchment area is a depression surrounding the side port. Some embodiments may also include an additional side port including a valve for switching between collecting colostrum using the side port to collecting milk using the additional side port.

In another aspect of the present disclosure, a funnel device for use in a system for collecting colostrum and/or milk from a breast may include: a body; a funnel shaped portion of the body having a first open end for contacting a breast; a predominantly cylindrical shaped portion of the body having a second open end for connecting to a source of suction; a side port between the first and second ends for connecting to a fluid collection device; a catchment area at or near the side port; and a blocking member between the side port and the second end, for preventing colostrum from passing beyond the side port and through the second end. Again, the blocking member may include at least one aperture for allowing suction force to be transmitted from the second end to the first end. The funnel device may include any of the features described above in relation to the adapter.

In another aspect of the present disclosure, a system for collecting colostrum and/or milk from a breast may include an adapter, a funnel device and a source of suction. The adapter may include any of the features described above. Optionally, the system may also include a syringe, connectable to the side port of the adapter. Alternatively, the system may include a tube, connectable to the side port, and a syringe, connectable to the tube. The source of suction may comprise a breast pump device.

In another aspect of the present disclosure, a method for collecting colostrum from a breast may involve: connecting a funnel device with a first end of an adapter; connecting a suction source with a second end of the adapter; connecting a collection device with a side port of the adapter; contacting an open end of the funnel device with the breast; activating the suction source to generate suction force through the adapter; collecting colostrum in a catchment area of the adapter; and moving the colostrum from the catchment area into the collection device. At least some of these steps may be performed in a different order without departing from the scope of the invention.

In some embodiments, the collection device comprises a syringe, and moving the colostrum from the catchment area into the collection device comprises retracting a plunger of the syringe. In some embodiments, connecting the adapter with a source of suction comprises connecting the second end of the adapter to a breast pump system. Some embodiments may further include collecting milk from the breast through an additional side port in the adapter, into an additional collecting device coupled with the additional side port. Such a method may also further include switching a valve from a first position, for collecting colostrum, to a second position, for collecting milk. The method may also further include preventing the colostrum from passing through the second end of the adapter with a blocking member disposed in the adapter between the side port and the second end.

In another aspect of the disclosure, a method for collecting colostrum from a breast may involve: connecting a small diameter end of a funnel device with a suction source; connecting a collection device with a side port of the funnel device; contacting an large diameter end of the funnel device with the breast; activating the suction source to generate suction force through the funnel device; collecting colostrum in a catchment area of the funnel device; and moving the colostrum from the catchment area into the collection device.

In some embodiments, connecting the funnel device with a source of suction comprises connecting the small diameter end of the funnel device to a breast pump system. Some embodiments may further include collecting milk from the breast through an additional side port in the funnel device or the suction source, into an additional collecting device coupled with the additional side port. Such embodiments may also include switching a valve from a first position, for collecting colostrum, to a second position, for collecting milk. Some embodiments may also include preventing the colostrum from passing through the small diameter end of the funnel device with a blocking member disposed in the funnel device between the side port and the second end.

In another aspect of the disclosure, an adapter for use in a system for collecting colostrum and/or breast milk may include: a body having a predominantly cylindrical shape; a first open end of the body for connecting to a funnel device; a second open end of the body for connecting to a source of suction; a blocking member inside the body, between the first open end and the second open end, for preventing colostrum from passing from the first open end through the second open end; an aperture in the blocking member to allow suction force applied at the second open end to generate suction at the first open end; a reservoir extending off of a side of the body, between the first open end and the blocking member, for containing the colostrum and/or breast milk, wherein the reservoir has a proximal end located at a junction of the reservoir with the side of the body and a distal end; and a port disposed on the distal end of the reservoir for connecting the adapter to a fluid collection device.

In some embodiments, the adaptor may have a one-piece construction. In some embodiments, the first open end and the second open end may have different inner diameters. In some embodiments, the blocking member may be a wall, and the aperture may be a hole through the wall. In some embodiments, the hole is located closer to an opposite side of the body of the adapter than to the side of the adapter off of which the reservoir extends. In some embodiments, the reservoir further includes fluid level markings for measuring an amount of the colostrum and/or breast milk in the reservoir.

In some embodiments, the first open end has an inner diameter sized to fit a narrow end of the funnel device within the first open end, and the second open end has an outer diameter sized to fit a connecting end of the source of suction over the second open end. In some embodiments, the fluid collection device is a syringe, and the port is configured to attached to one end of the syringe. In various embodiments, the funnel device may be any suitable funnel or breast shield.

In another aspect of the disclosure, a method for collecting colostrum from a breast may involve: receiving colostrum expressed from the breast into an open end of a funnel device that is connected at an opposite end to a first end of an adapter; applying a first suction force at a second end of the adapter, using a suction source connector coupled with the second end of the adapter, where the first suction force is transmitted through an aperture in a blocking member inside the adapter to facilitate movement of the colostrum through the funnel and into the adapter; using the wall in the adapter to prevent the colostrum from passing through the second end of the adapter and direct the colostrum into a reservoir extending off of a side of the adapter; allowing the colostrum to collect in the reservoir; applying a second suction force to a port on the reservoir, using a colostrum collection device attached to the port; and allowing the colostrum to pass out of the reservoir and into the colostrum collection device, in response to the second suction force.

In some embodiments, the funnel device is a breast shield, and the method may further include contacting the open end of the breast shield with the breast before applying the first suction force. Some embodiments may further involve measuring a fluid level of the colostrum in the reservoir by viewing the colostrum and a fluid level marker on a side of the reservoir. Some embodiments may further involve removing the collection device from the port, after the colostrum has passed into the collection device, and delivering the colostrum directly to a newborn from the collection device, without passing the colostrum into any additional device. In some embodiments, applying the first suction force involves turning on a breast pump device coupled with the second end of the adapter. In some embodiments, the collection device is a syringe, and applying the second suction force involves retracting a plunger of the syringe.

In another aspect of the disclosure, an adapter system for facilitating collection of colostrum from a breast may include an adapter, a removable reservoir and a hand-expression funnel. The adapter may include a first open end for connecting to a breast shield of a breast pump system, a second open end for connecting to a breast pump connector of the breast pump system, and a third open end, disposed between the first and second open ends, for allowing the colostrum to pass out of the adapter, The removable reservoir may include a wide end for removably attaching to the third open end and a narrow end for attaching to a colostrum delivery device. The hand-expression funnel may include a wide end for receiving colostrum and a narrow end for attaching to the colostrum delivery device.

In some embodiments, the adapter may also include a cylindrical body, between the first and second open ends, a blocking member inside the body, between the second open end and the third open end, for directing the colostrum through the third open end, and an aperture in the blocking member to allow suction force applied at the second open end to generate suction at the first open end. The blocking member, for example, may include a wall, and the aperture may include a hole through the wall. In some embodiments, the hole is located closer to a top of the adapter than to a bottom of the adapter. In some embodiments, the first open end has a first inner diameter that is larger than a second inner diameter of the second open end.

The removable reservoir and/or the hand-expression funnel may each optionally include fluid level markings for measuring an amount of the colostrum. In some embodiments, the colostrum delivery device is a syringe. The narrow end of the removable reservoir may optionally include threads on its inner surface for coupling with outer threads on the syringe. The wide end of the removable reservoir may also optionally include threads on its inner surface for coupling with outer threads on the third open end of the adapter. The narrow end of the hand-expression funnel may also include threads on its inner surface for coupling with outer threads on the syringe.

The adapter system may include any number of components. For example, in one embodiment, the system includes a least one additional adapter and at least one additional removable reservoir, to allow a woman to breast pump both breasts simultaneously.

In another aspect of the disclosure, a method for collecting colostrum from a breast and delivering the colostrum to a newborn may involve: attaching an adapter with a removable reservoir to a breast pump shield at one end and a breast pump connector at an opposite end; attaching the removable reservoir with a syringe; expressing colostrum from the breast, into the removable reservoir; drawing the colostrum into the syringe by pulling back a plunger of the syringe; detaching the syringe from the removable reservoir; and delivering the colostrum to the newborn directly from the syringe. Optionally, the method may further involve hand-expressing colostrum from the breast into a funnel attached to an additional syringe; drawing the colostrum into the syringe by pulling back a plunger of the additional syringe; detaching the additional syringe from the funnel; and delivering the colostrum to the newborn directly from the additional syringe. The method may also optionally include measuring a fluid level of the colostrum in the funnel by viewing the colostrum and a fluid level marker on a side of the funnel. In some embodiments, after the detaching step and before the delivering step, the method may involve: attaching the syringe to a funnel; hand-expressing colostrum from the breast into a funnel; drawing the colostrum into the syringe by pulling back the plunger of the syringe; and detaching the syringe from the funnel.

These and other aspects and embodiments are described in further detail below, in relation to the attached drawing figures.

BRIEF DESCRIPTION OF THE DRAWINGS

FIGS. 1A-1C are an end-on, cross-sectional perspective, and perspective views, respectively, of a funnel for capture of milk and/or colostrum, according to one embodiment;

DETAILED DESCRIPTION

Figure 2B:
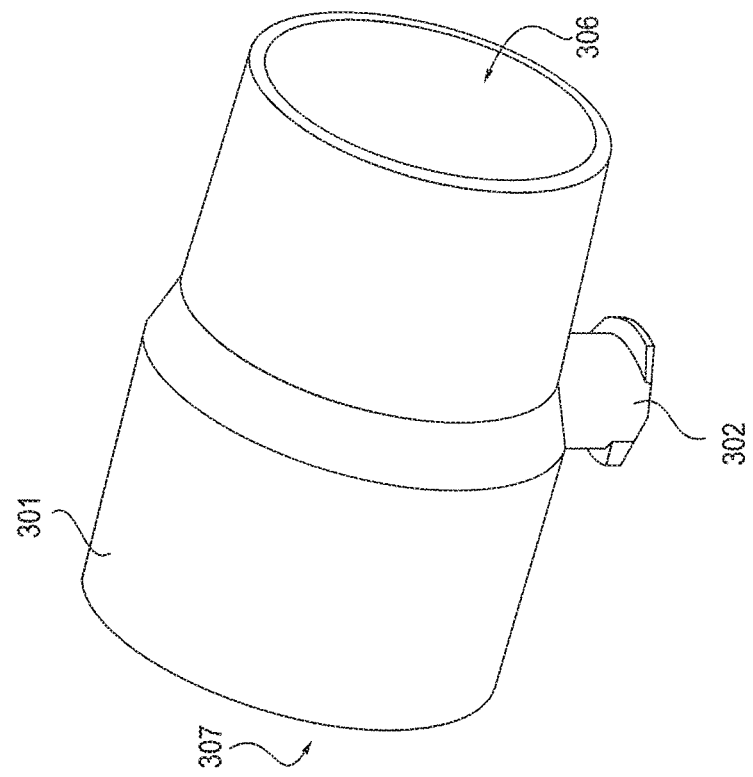
FIGS. 2A and 2B are cross-sectional and side views, respectively, of a milk and colostrum collection funnel adapter with a catchment area and connector to a dispensing device, according to one embodiment.

The embodiments described below are generally designed to facilitate collection and delivery of colostrum from a female breast. In some or all embodiments, the systems and devices described herein may also be used to collect and/or deliver breast milk. However, many or all of the embodiments may include features, such as reservoirs, receptacles, funnels, or the like, which are configured primarily for colostrum. For example, these features may be sized in such a way as to be specifically beneficial for the very small volumes of colostrum produced by the breast. In any event, whether a system is referred to as a "colostrum collection system" or a "colostrum and milk collection system," any or all embodiments may be used, or adapted for use, for facilitating collection and/or delivery of colostrum and/or breast milk.

All figures either depict components in isolation or with breast pump accessory attachments or funnels, for use with a vacuum style breast milk pump that is hand powered or machine powered. The system is operable with suction and attachment to a breast to express the milk or colostrum through a funnel contacted to the breast. Embodiments allow for the capture of colostrum or milk into a collection device, which is then detached from the remainder of the system in order to deliver the milk or colostrum to the newborn, infant, or baby. In various exemplary embodiments, the components of a device or system may press fit together, glide, screw in, or otherwise attach. In addition, in some embodiments, some components may rotate or glide and experience varying degrees of frictional resistance.

FIGS. 1A-1C are end-on, cross-sectional perspective, and perspective views, respectively, of a funnel 100 for capture of milk and/or colostrum, according to one embodiment. Funnel 100 may have a shape, size and overall configuration similar to any funnel or breast shield, but is includes additional features to facilitate the collection of colostrum. Funnel 100 may include a wide end 101, a narrow end 110 and a block 102 (or "wall") between the two ends 101, 110. Block 102 may include one or more apertures 104 (or "holes" or "openings"), to allow suction force to pass through the block 102 and thus to help draw milk and/or colostrum into the funnel 101. Funnel 100 may also include a trough 106 (or "indentation" or "channel"), which together with block 102 forms a catchment area 107. A port 108 is located at the bottom of catchment area 107, for connecting with a milk/colostrum collection and dispensing device, such as but not limited to a syringe. The phrase "catchment area" is used herein to generally describe an area or portion of funnel 100 (or of other devices in other embodiments) that is configured to capture breast milk and/or colostrum and/or guide the flow of breast milk and/or colostrum through the device in a desired direction. In the embodiment of FIGS. 1A-1C, as best seen in FIG. 1B, catchment area 107 is generally bounded by block 102 and trough 106, with port 108 located at the bottom. Funnel 100 may be made of any suitable material, such as any suitable polymer or metal.

In use, breast milk and/or colostrum is expressed into wide end 101 of funnel 100. Suction force may be applied at narrow end 110 of funnel 100, and such force will pass through aperture 104, to help drawing milk and/or colostrum through wide end 101. Block 102 helps to block the milk and/or colostrum from passing through narrow end 110 and instead directs the milk and/or colostrum into catchment area 107 and thus through port 108. Trough 106 may also assist in directing milk and/or colostrum toward port 108. A syringe or other collection/delivery device (not shown) may then be used to draw the milk and/or colostrum through port 108 into the device, so that it can be delivered to a newborn. Port 108 may have any suitable configuration for connection to a collection/delivery device, such as but not limited to a luer connector, screw/threaded connector, press fit connector, or a combination thereof, to provide multi-connector functionality to work with multiple collection/delivery devices.

Figure 2A:
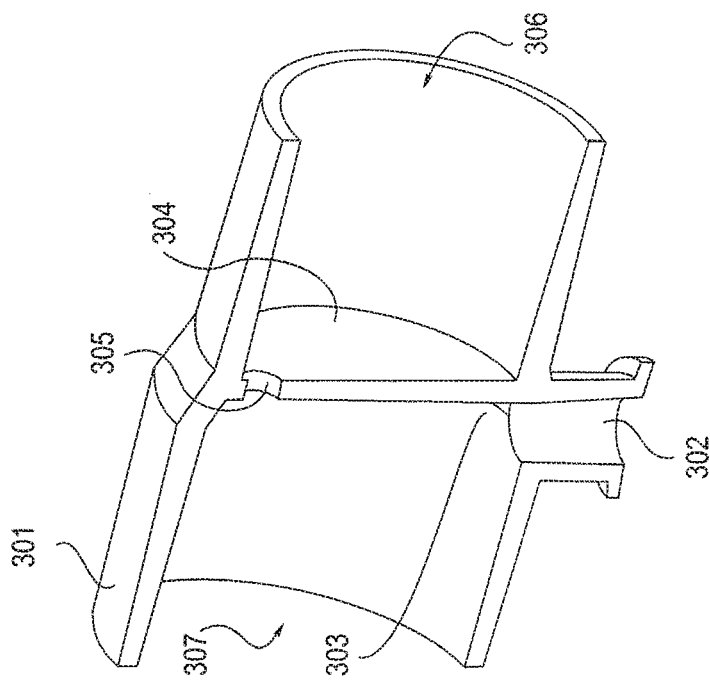

FIGS. 2A and 2B are cross-sectional perspective and perspective views, respectively, of an adapter 301 for facilitating the collection of breast milk and/or colostrum, according to one embodiment. Adapter 301 may include a front end 307 for connecting to a collection mechanism, such as a funnel/breast shield, and a back end 306 for connecting to a flow driver source, such as a vacuum pump (or "breast pump"). Either of the two ends 307, 306 may be configured to either fit within or over a corresponding end of a device with which it connects. In other words, in some embodiments front end 307 may fit over a narrow end of a funnel/breast shield, while in alternative embodiments front end 307 may fit inside of a narrow end of a funnel/breast shield. Similarly, back end 306 may fit within a connecting end of a breast pump connector in some embodiments and may fit over a connecting end of a breast pump connector in other embodiments. Adapter 301 may also include a port 302 for connecting to a collection/delivery device, such as a syringe. A block 304 forms a catchment area 303 and helps direct milk and/or colostrum into port 302. Block 304 may also include an aperture 305, which allows flow-directing force, such as suction, to pass through. Port 302 may have any suitable configuration for connection to a collection/delivery device, such as but not limited to a luer connector, screw/threaded connector, press fit connector, or a combination thereof, to provide multi-connector functionality to work with multiple collection/delivery devices. Adapter 301 may be made of any suitable material, such as any suitable polymer or metal.

Figure 3:
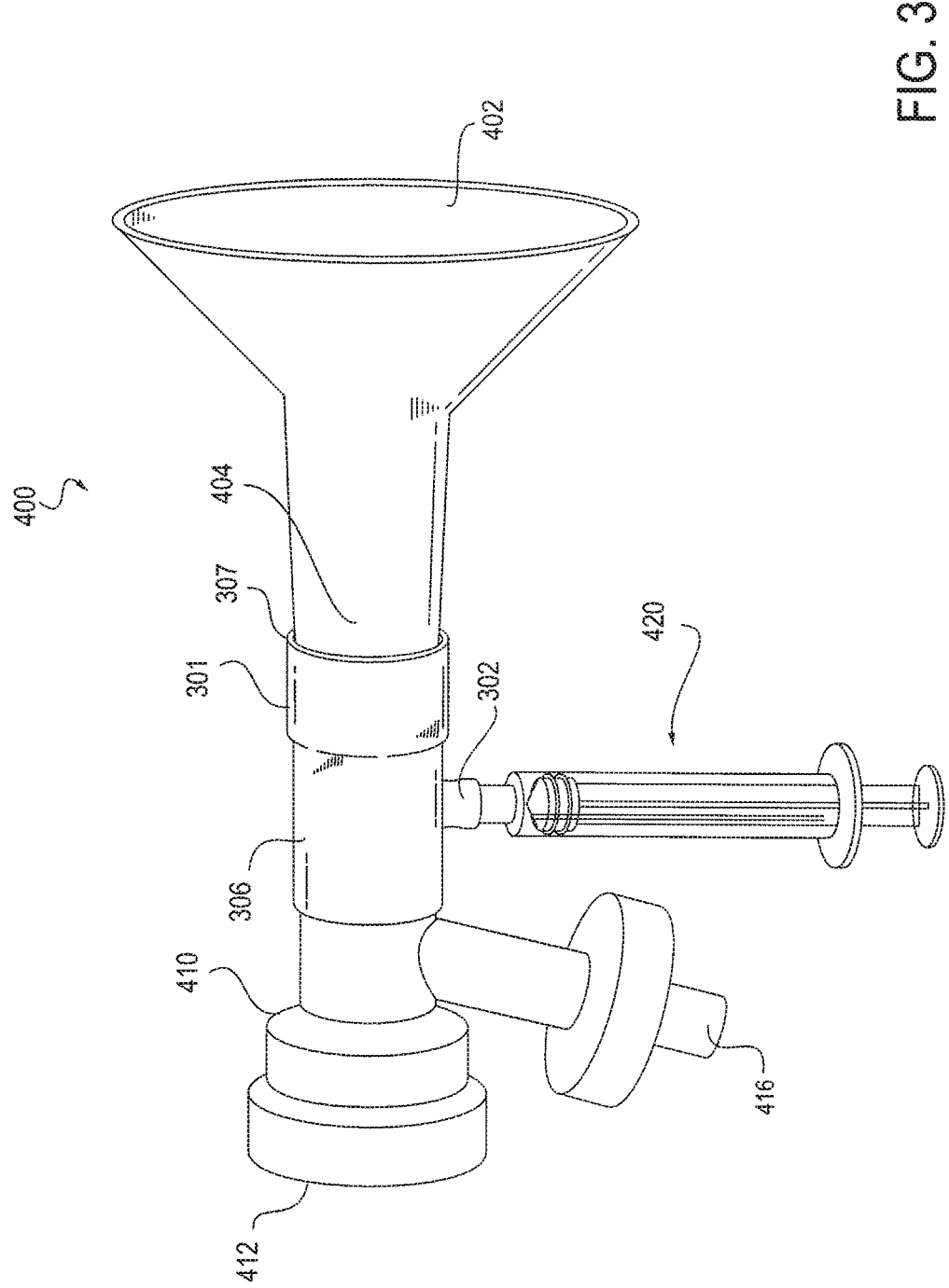
FIG. 3 is a side view of a milk and colostrum collection system including an adapter, funnel, breast pump connector and collection/delivery device, according to one embodiment.

FIG. 3 is a side view of one embodiment of a system 400 for collecting and dispensing breast milk and/or colostrum to a newborn. System 400 includes adapter 301, a funnel 401, a breast pump connector 410 (or "vacuum pump connector"), and a syringe 420 (which may be substituted by another collection/delivery device in an alternative embodiment). A narrow end 404 of funnel 401 is inserted into front end 307 of adapter 301, leaving a wide end 402 of funnel 401 open, for allowing milk and/or colostrum to pass into funnel 401. Funnel 401 may be any suitable funnel or breast shield that is currently available or hereafter invented, and the term "funnel" is intended herein to mean "funnel or breast shield." In other words, the terms "funnel" and "breast shield" are used interchangeably herein. One end of breast pump connector 410 is inserted into back end 306 of adapter 301. Breast pump connector 401 may include a suction connection 412 for connecting to a source of vacuum/suction (not shown), such as but not limited to a breast pump machine. Breast pump connector 401 may also include a collection device connection 414 for connecting to a larger collection device (not shown), such as but not limited to a bottle for containing breast milk. Collection device connection 414 may include a one-way valve 416. Syringe 420 may be connected to adapter 301 via port 302, as described above.

In use, colostrum (or alternatively breast milk) may be expressed into wide end 402 of funnel 401. Suction applied through system 400 via suction connection 412 and aperture 305 in adapter 301 (not visible in FIG. 3) may help draw the colostrum toward port 302. The plunger of syringe 420 may then be retracted to suck the colostrum into the barrel of syringe 420, where the colostrum may be stored for any desired length of time. Finally, the colostrum may be delivered directly to a newborn from syringe 420 (by mouth or via a tube into the nose, for example). Syringe 420 may be used to collect small quantities of liquid and/or more viscous liquid, such as but not limited to colostrum, or it may be used to periodically sample small quantities from the flow stream into the larger container. Typically, syringe 420 will be coupled with port 302 with the plunger of syringe 420 fully inserted into the barrel, so that there is limited free volume within the barrel. Then, after expression of colostrum and/or milk, the syringe plunger is pulled back to allow for expelled material in catchment area 303 of adapter 301 to be drawn into the syringe 420. Alternatively, syringe 420 may be pre-filled with air before attaching it to port 302, and may then be used to force air into funnel 401, to build positive pressure and thus facilitate detachment of the breast from the suction force generated between wide end 402 of funnel 401 and the breast.

In various embodiments, system 400 may be provided as only a subset of the devices depicted in FIG. 3. For example, in one embodiment, system 400 may include only adapter 301 and funnel 401. Syringe 420 and breast pump connector 410 may be provided separately by a user. In another embodiment system 400 may include adapter 301, funnel 401 and breast pump connector 410, and syringe 420 may be provided separately. Thus, system 400 may include any suitable combination of the devices illustrated in FIG. 3. This is true of alternative system embodiments described below and will not be repeated for each embodiment.

Figure 4:
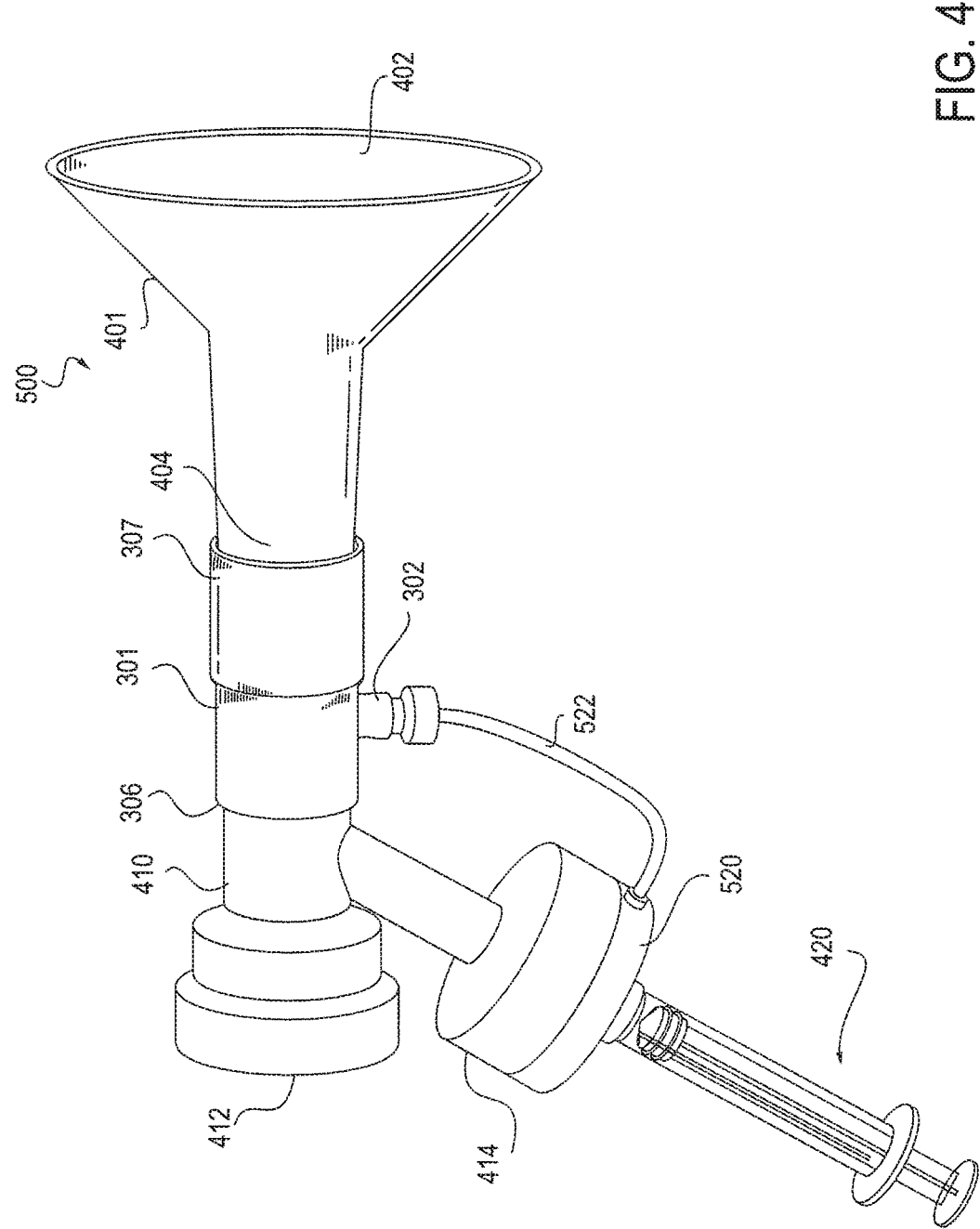
FIG. 4 is a side view of a milk and colostrum collection system including an adapter, funnel, breast pump connector and collection/delivery device, according to an alternative embodiment.

FIG. 4 is a side view of an alternative embodiment of a system 500 for collecting and dispensing breast milk and/or colostrum. Adapter 301, funnel 401, breast pump connector 410 and syringe 420 are the same as in the embodiment described in FIGS. 2A, 2B and 3, so will not be described again. In this embodiment, however, system 500 includes the additional components of a second adapter 520 and a bypass tube 522. Second adapter 520 attaches to collection device connection 414 of breast pump connector 410, and bypass tube 522 attaches at one end to port 302 of adapter 301 and at an opposite end to second adapter 502. In use, colostrum and/or breast milk passes through funnel 401, into adapter 301, through port 302 and bypass tube 522, and into second adapter 520. Finally, the colostrum and/or milk is sucked into syringe 420 for containment and delivery. Bypass tube 507 allows the suction force generated by system 500 to pull pooled colostrum/milk into syringe 420 without having to pass through one-way valve 416 (visible in FIG. 3) of connection 414.

Figure 5:
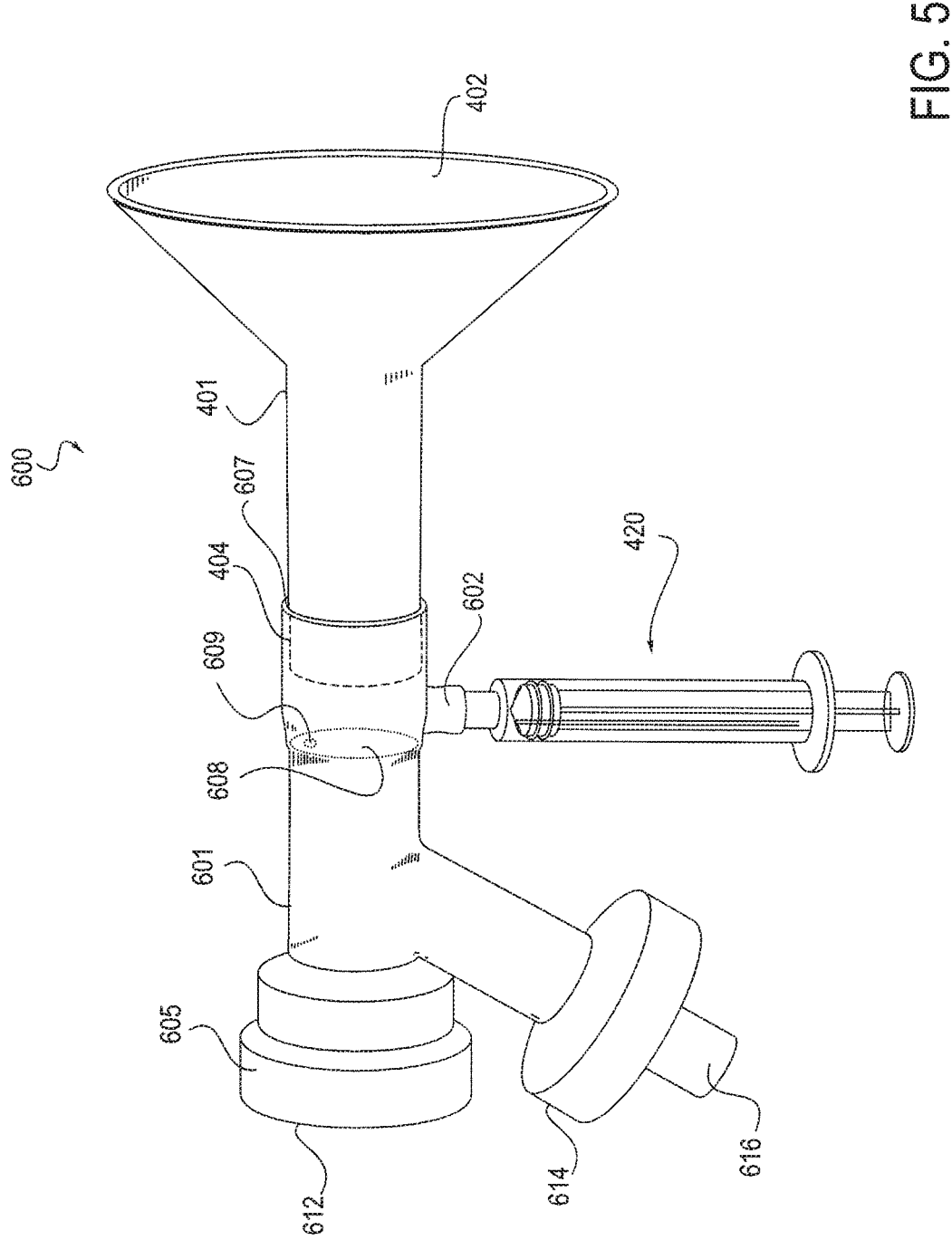
FIG. 5 is a side view of a milk and colostrum collection system including a combined adapter/breast pump connector, funnel, and collection/delivery device, according to another alternative embodiment.

FIG. 5 is a side view of another alternative embodiment of a system 600 collecting and dispensing colostrum and/or breast milk. In this embodiment of system 600, funnel 401 and syringe 420 are the same as previously described in reference to FIGS. 3 and 4. This embodiment, however, includes a one-piece, combination adapter/breast pump connector 601 (referred to herein as "combination adapter 601"). Combination adapter 601 includes a front end 607, for connecting with narrow end 404 of funnel 401, a block 608 with an aperture 609, and a port 602 for connecting with syringe 420. Combination adapter 601 also includes a suction connection 612 and a collection device connection 614 with a one-way valve 616. Essentially, combination adapter 601 combines the functions of adapter 301 and breast pump connector 410 of the embodiment in FIG. 3. Again, block 608 (or "wall" or "inner wall") and aperture 609 allow suction force to pass through system 600 while preventing colostrum and/or breast milk expressed from the breast from passing through suction connection 414 and instead directing it through port 602 into syringe 420.

As illustrated in FIG. 5, front end 607 of adapter 601 may be slightly wider than an immediately adjacent tubular portion of adapter 601, sized and configured so that funnel 401 (or "breast shield") may be inserted into it. In some embodiments, funnel 401 may fit into the front end 607 via a press fit connection. In alternative embodiments, the funnel 401 may attach to front end=607 via threads or any other suitable connection means.

Syringe 420 (or "collection/delivery device") may be used to collect small quantities of liquid and/or more viscous liquid, such as but not limited to colostrum, and/or it may be used to periodically sample small quantities from the flow stream into the larger container. In various embodiments, any suitable size of syringe 420 may be used as a collection/delivery device. Also, as mentioned above, other types of collection/delivery devices may alternatively be used.

Figure 6A:
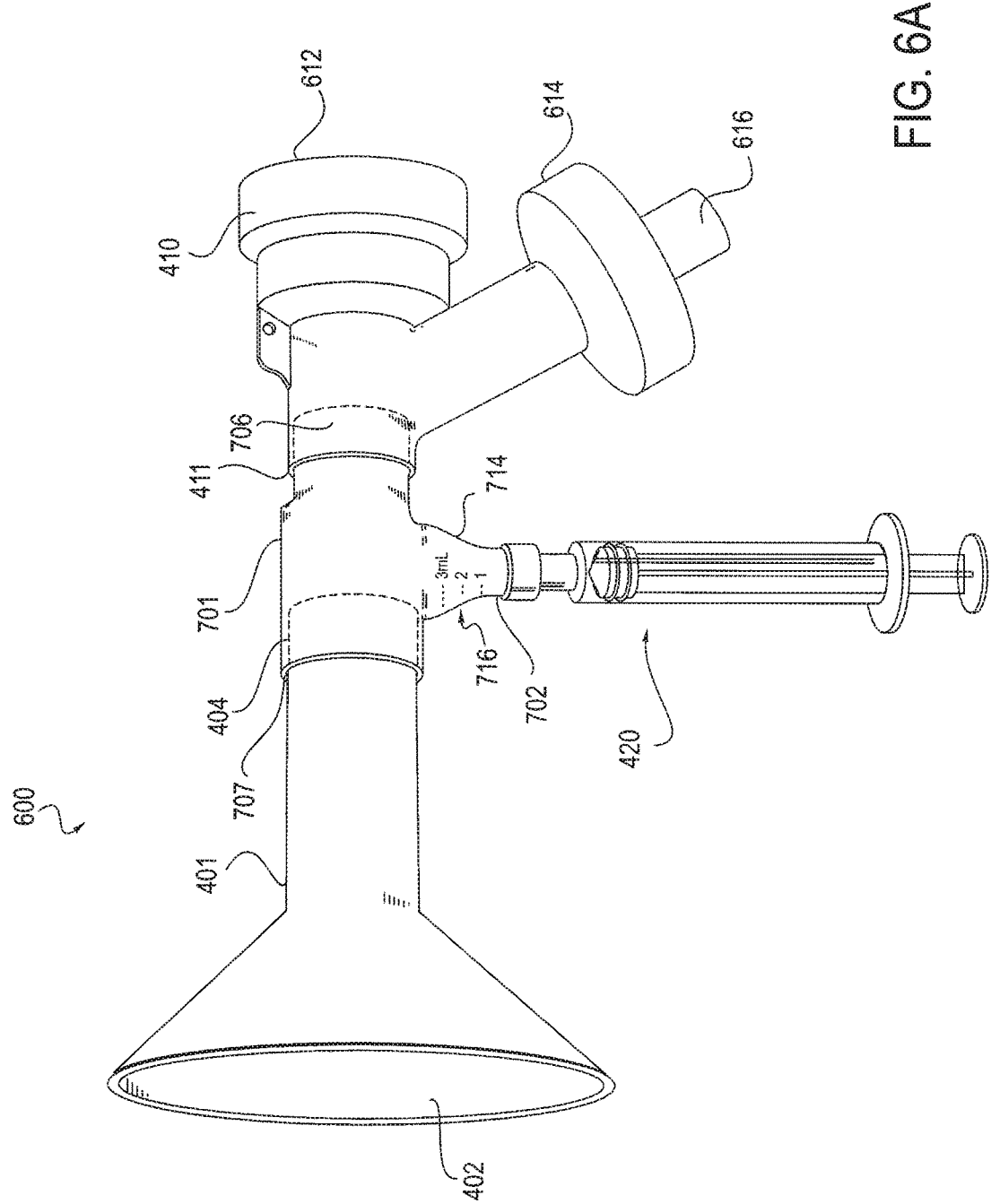
FIG. 6A is a side view of a milk and colostrum collection system including an adapter, funnel, breast pump connector and collection/delivery device, according to another alternative embodiment.
Figure 6B:
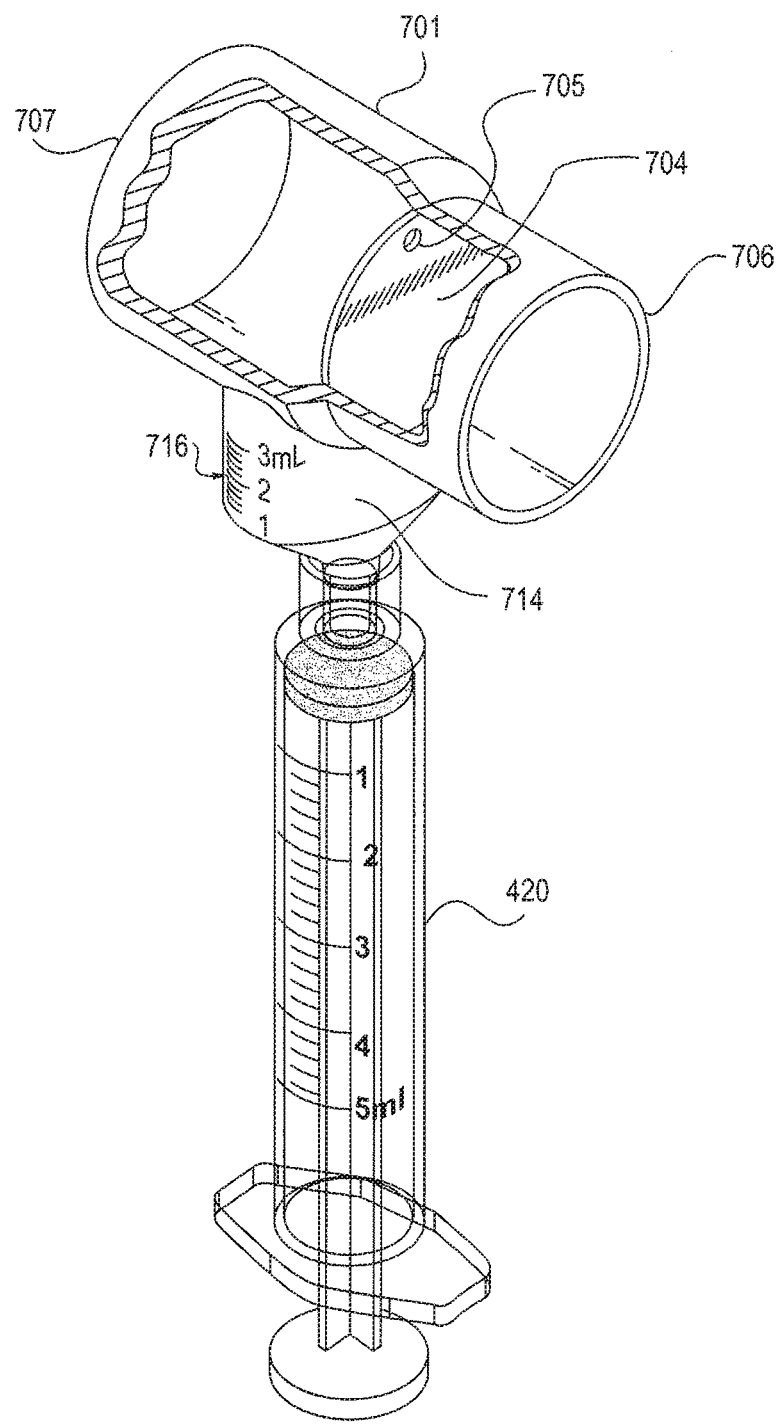
FIG. 6B is a perspective view of the adapter and syringe of FIG. 6A.
Figure 6C:
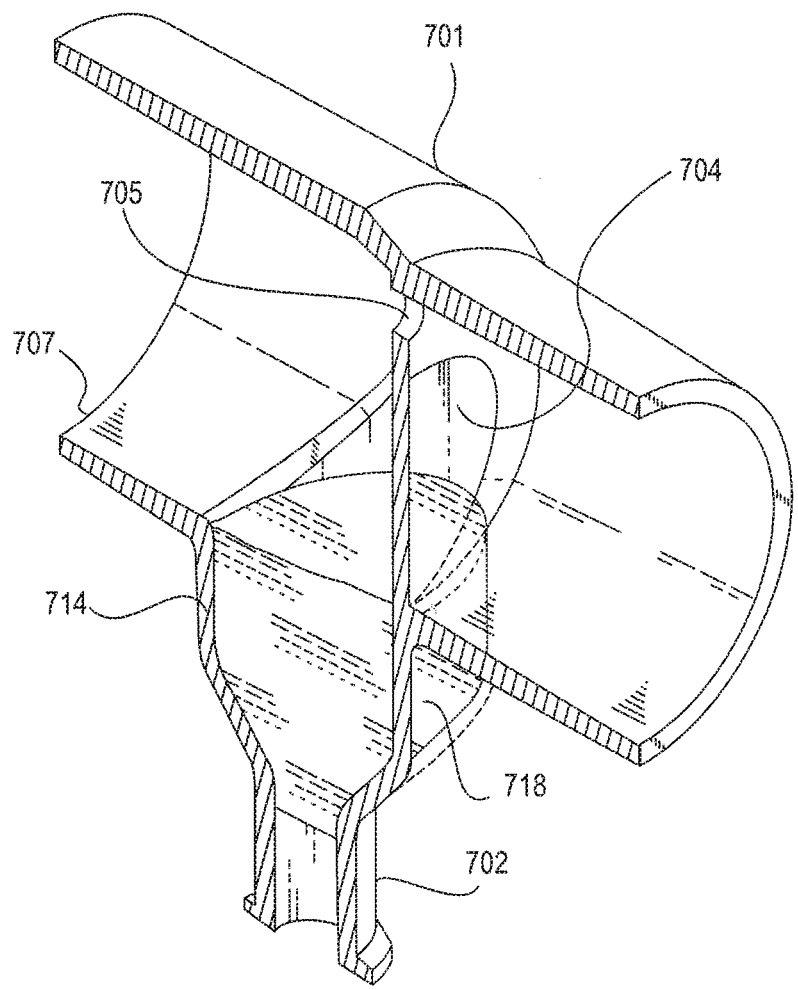
FIG. 6C is a cross-sectional, perspective view of the adapter of FIGS. 6A and 6B.

FIGS. 6A-6C are a side view of a colostrum/milk collection and delivery system 700, a perspective view of an adapter 701 and syringe 420 of system 700, and a cross-sectional, perspective view of adapter 701, according to another alternative embodiment. System 700 may include adapter 701, funnel 401, breast pump connector 410 and syringe 420. As mentioned previously, in some embodiments, adaptor 701 may be provided by itself as a device, and funnel 401, breast pump connector 410 and syringe 420 may be provided separately. In another embodiments, adaptor 701 and syringe 420 may be provided as a system. In various embodiments, any suitable combinations of the components of system 700 may be provided together or separately. Thus, the scope of the invention is not limited by any one combination of system components. As funnel 401, breast pump connector 410 and syringe 420 are the same as described above in reference to FIG. 3, they will not be described again here. One difference of note is that an adapter end 411 of breast pump connector 410 fits over a back end 706 of adapter 701, whereas previous exemplary embodiments illustrated the adapter fitting over the breast pump connector. The embodiment of FIG. 6A illustrates the fact that in various alternative embodiments the various components may connect with the adapter in multiple different ways, as mentioned previously. In fact, in some embodiments, adapter 701 may be able to connect with some embodiments of breast pump connector 410 by fitting within them, as shown in FIG. 6A, and with other embodiments by fitting over them. The same is true at a front end 707 of adapter and its fit with narrow end 404 of funnel 401.

Referring now to FIGS. 6B and 6C, adapter 701, in this embodiment, includes a block 704 (or "wall"), an aperture 705 and a port 702, as in previous embodiments. The primary difference between adapter 701 and previously described adapters is the addition of a reservoir 714 below the main, tubular portion of adapter 701. Reservoir 714 may help to concentrate and/or collect colostrum 718 (shown in FIG. 6C—alternatively breast milk) and direct it to port 702. Reservoir 714 also may help contain the colostrum and/or breast milk and thus help prevent it from spilling back out of adapter 701 in the wrong direction (i.e., toward the user). In some embodiments, as illustrated, reservoir 714 may include level markers 716 for measuring the volume of fluid collected in reservoir 714. Level markers 716 may be in milliliters or any other suitable gradation.

Figure 7:
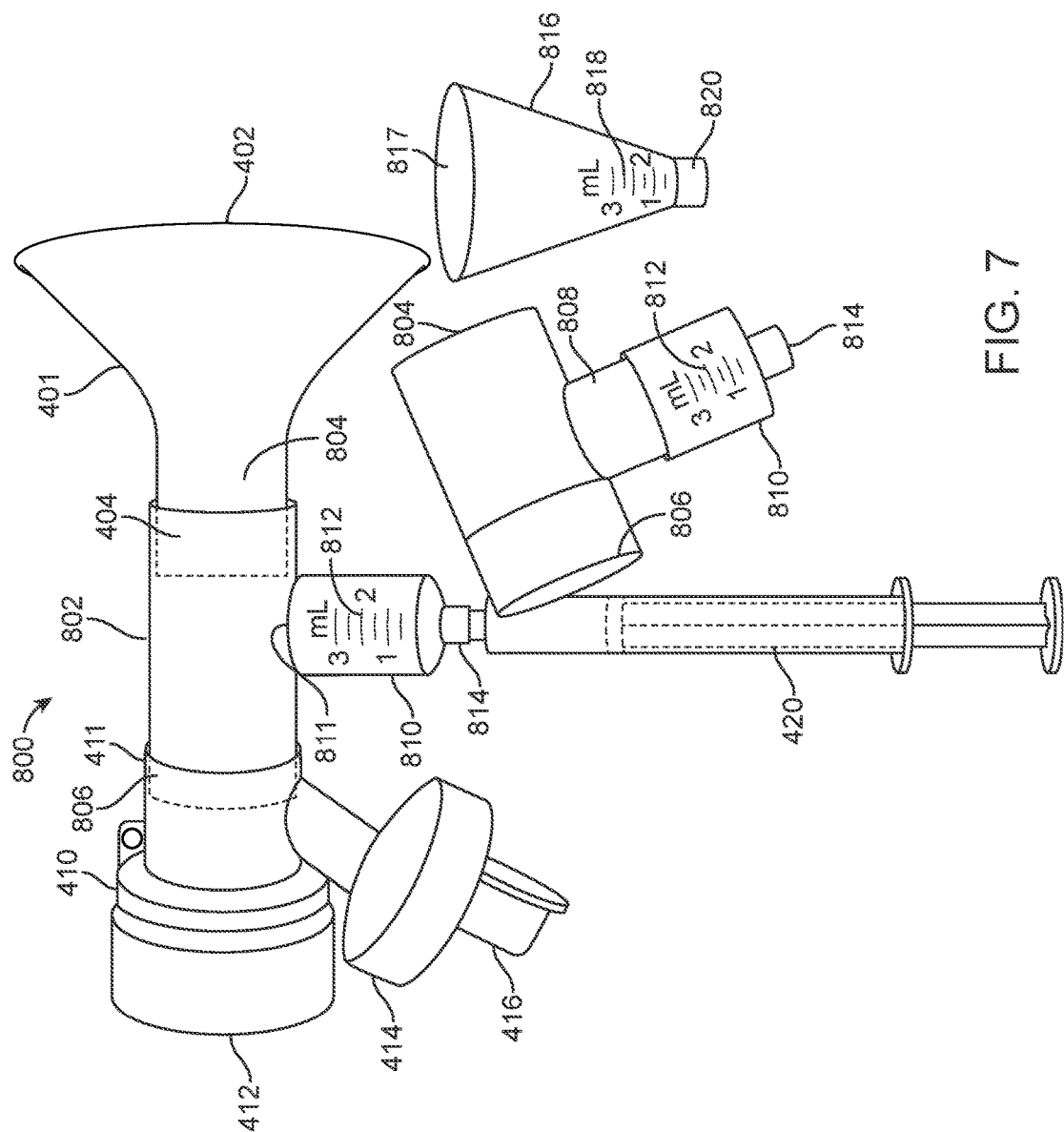
FIG. 7 is a side perspective view of a colostrum collection system, according to another alternative embodiment.

FIG. 7 is a side view of a colostrum collection and delivery system 800 (or "adapter system"), according to another alternative embodiment. Although this embodiment is described as a "colostrum collection and delivery system," the embodiment may also be used for collection and delivery of breast milk. As mentioned above, this is true of any of the above-described systems and devices, regardless of whether they are called "colostrum collection systems," "milk/colostrum collection systems" or other similar monikers. As funnel 401 (or "breast shield"), breast pump connector 410 and syringe 420 are the same as described above in reference to FIG. 3, they will not be described again here. As mentioned previously, any suitable funnel 401, breast pump connector 410 and syringe 420 may be used, and multiple different sizes, shapes, and brands of these components may be compatible with system 800, according to various embodiments. In some embodiments, system 800 may include one or more syringes 420 and/or funnels 401, while in other embodiments, system 800 may be provided without these components.

In the illustrated embodiment, system 800 includes an adapter 802, a removable reservoir 810 and a hand-expression funnel 816. In some embodiments, system 800 may be provided with two adapters 802, two reservoirs 810 and one funnel 816, to allow the woman to double pump (i.e., express colostrum from both breasts at the same time with two breast pump shields). Alternative embodiments of system 800 may include different numbers and/or combinations of components, different sizes and shapes of adapter 802, reservoir 810 and/or funnel 816, and/or the like. Adapter 802, in this embodiment, is a generally T-shaped adapter 802, with three open ends: a funnel connecting end 804, a breast pump connecting end 806 and a dispensing end 808. The interior portion of adapter 802, which is described in more detail in relation to FIGS. 10A-10D, may be the same as or similar to that shown in FIGS. 6B and 6C. However, unlike the embodiment of FIGS. 6A-6C, in this embodiment adapter 802 does not include a built-in reservoir. Instead, dispensing end 808 of adapter 802 is designed to connect with removable reservoir 810.

Removable reservoir 810 has a wide end 811 for connecting with dispensing end 808 of adapter 802, a narrow end 814 for connecting with syringe 420, and multiple level indicators 812 to help a user determine how much colostrum resides within reservoir 810. Funnel 816 includes a wide end 817 for collecting colostrum that is hand expressed from the breast, a narrow end 820 for connecting with syringe 420, and multiple level indicators 816 to help a user determine how much colostrum resides within funnel 816. During use, the user may choose to collect colostrum using a breast pump with adapter 802 and reservoir 810, or using hand expression into funnel 816. The best practice for colostrum collection may often be to alternate between breast pump expression and hand expression. Reservoir 810 and funnel 816 are both designed to connect to syringe 420. As described above, syringe 420 is used to generate suction force to draw colostrum out of reservoir 810 or funnel 816. Once colostrum is pulled into syringe 420, syringe 420 may be detached and positioned in a newborn's mouth to directly deliver the colostrum to the newborn.

Figure 8E:
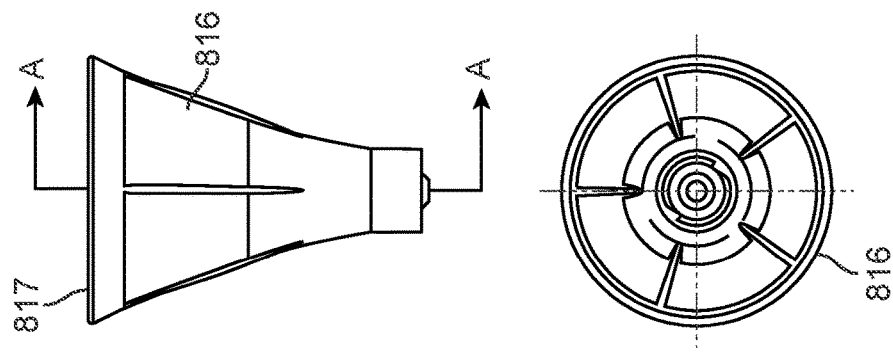
FIGS. 8A-8E are various alternative views of a funnel of the colostrum collection system of FIG. 7.
Figure 8D:
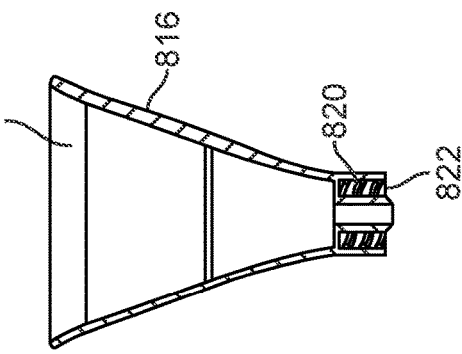
Figure 8C:
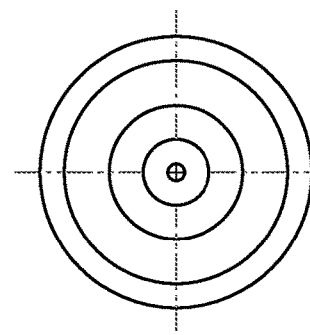
Figure 8A:
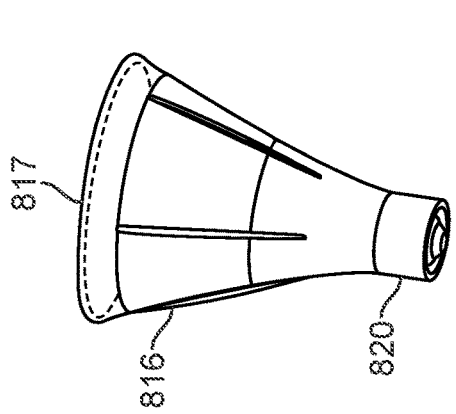
Figure 8B:
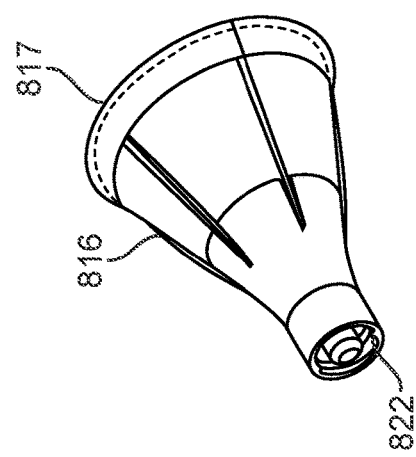

FIGS. 8A-8E are perspective (FIGS. 8A and 8B), top (FIG. 8C), side/cross-sectional (FIG. 8D), and bottom (FIG. 8E) views of funnel 816. As seen in FIGS. 8B and 8D, narrow end 820 includes inner threads 822 in this embodiment, for mating with outer threads on a connection end of a syringe. Alternatively, narrow end 820 may slide or press fit onto a connection end of a syringe or may connect with a syringe in any other suitable manner. In some embodiments, system 800 may include multiple different funnels 816, each providing a different connection mechanism at narrow end 820, to accommodate different types of syringe connections. Funnel 816 may also have any suitable dimensions. The embodiment of FIGS. 8A-8E is only one exemplary embodiment, however, and should not be interpreted as limiting the scope of the invention.

Figure 9E:
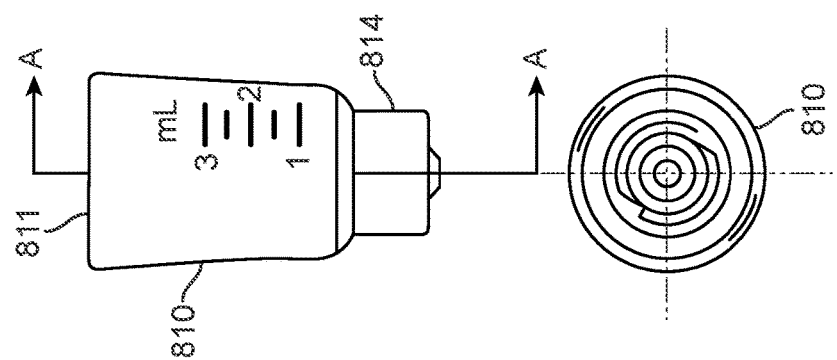
FIGS. 9A-9E are various alternative views of a receptacle of the colostrum collection system of FIG. 7.
Figure 9C:
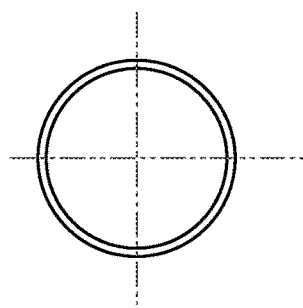
Figure 9D:
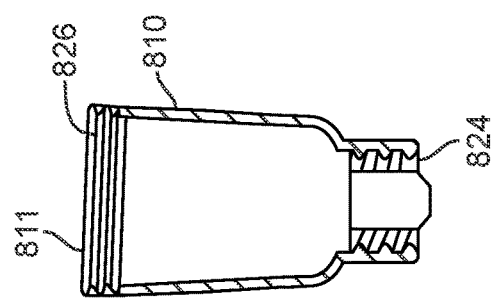
Figure 9A:
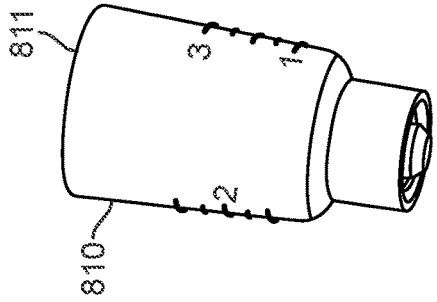
Figure 9B:
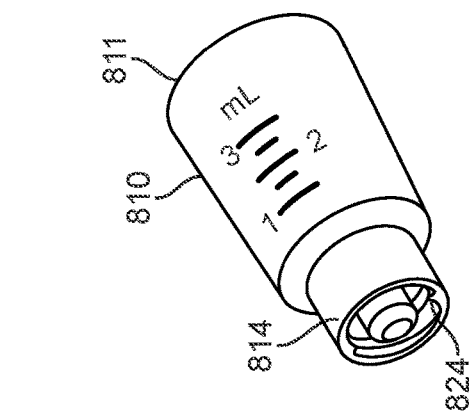

FIGS. 9A-9E are perspective (FIGS. 9A and 9B), top (FIG. 9C), side/cross-sectional (FIG. 9D), and bottom (FIG. 9E) views, respectively, of removable reservoir 810. As seen in FIGS. 9B and 9D, narrow end 814 includes inner threads 824 in this embodiment, for mating with outer threads on a connection end of a syringe. Alternatively, narrow end 814 may slide or press fit onto a connection end of a syringe or may connect with a syringe in any other suitable manner. In some embodiments, system 800 may include multiple different receptacles 810, each providing a different connection mechanism at narrow end 814, to accommodate different types of syringe connections. As visible in FIG. 9D, wide end 811 of reservoir 810 may also include inner threads 826, for connecting with outer threads on dispensing end 808 of adapter 802 (see FIGS. 10A-10D). As with narrow end 814, wide end 811 may alternatively fit onto adapter 810 by sliding or press fit or any other suitable connection mechanism. Reservoir 810 may also have any suitable dimensions. The embodiment of FIGS. 9A-9E is only one exemplary embodiment, however, and should not be interpreted as limiting the scope of the invention.

Figure 10C:
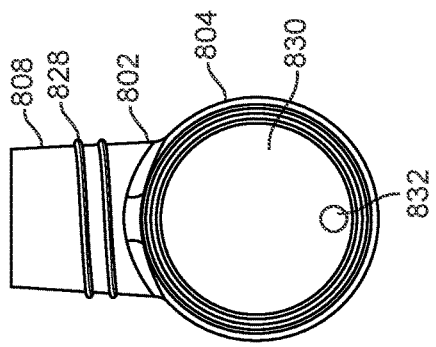
FIGS. 10A-10D are various alternative views of an adapter of the colostrum collection system of FIG. 7.
Figure 10D:
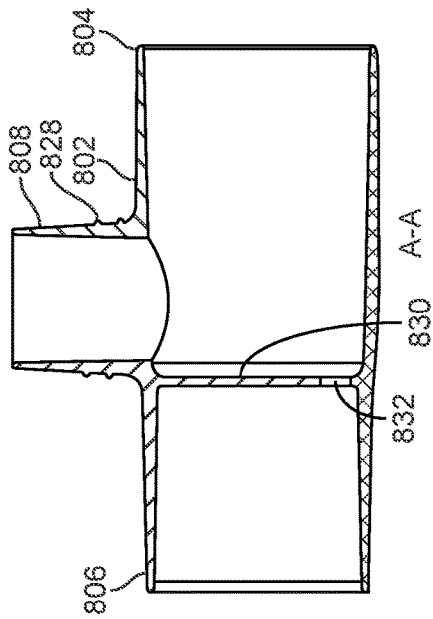
Figure 10A:
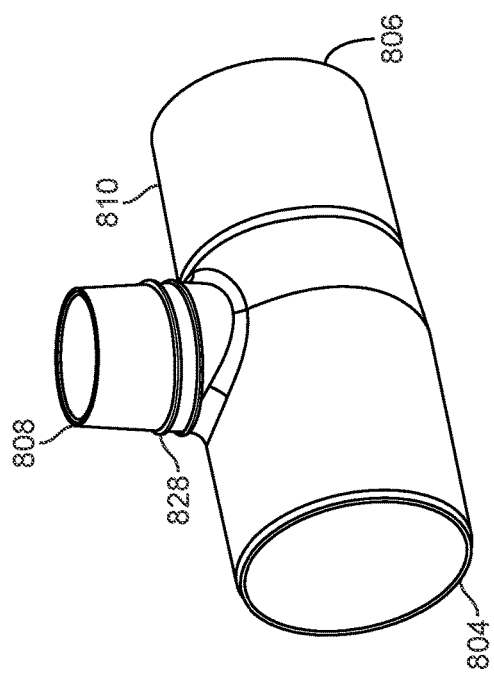
Figure 10B:
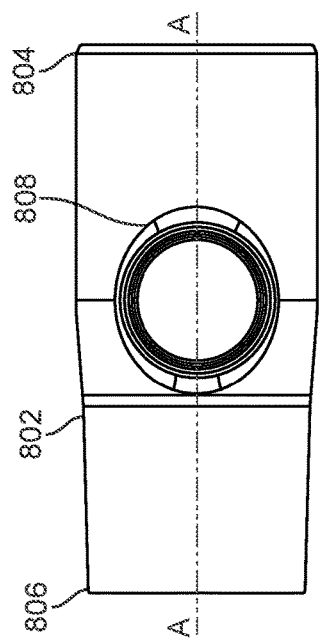

FIGS. 10A-10D are perspective, top, end, and side/cross-sectional views, respectively, of adapter 802. As best seen in FIGS. 10A, 10C and 10D, dispensing end 808 may include outer threads 828 for mating with reservoir 810, in some embodiments. As illustrated in FIGS. 10C and 10D, adapter 802, in this embodiment, includes a wall 830 with an aperture 832. Wall 830 is configured to direct colostrum (and/or milk) down through dispensing end 808. Aperture 832 allows suction force to be applied through adapter 802 while still allowing wall 830 to direct fluid (colostrum) in the direction of dispensing end 808.

According to various embodiments, adapter 802, reservoir 810 and funnel 816 may be made of any suitable material, such as any hard plastic, metal, polymer or the like. In one embodiment, for example, adapter 802, reservoir 810 and funnel 816 are made of a biocompatible, hydrophobic polypropylene. System 800 will typically be disposable, but in some embodiments it may be sterilizable and reusable.

Figure 11A:
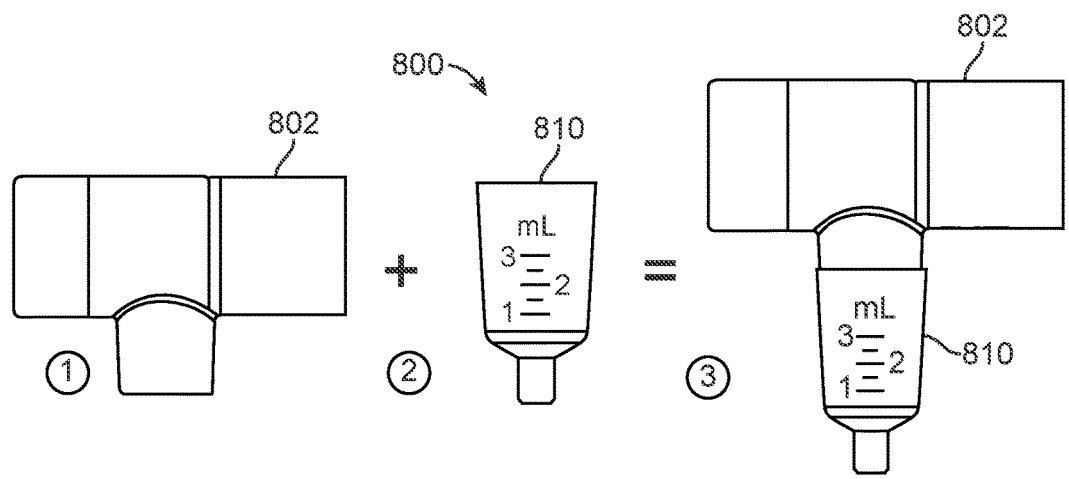
FIG. 11A is a side view of an adapter and a removable reservoir of a colostrum collection system, according to one embodiment.

Referring now to FIGS. 11A-11D, colostrum collection and delivery system 800 is shown again, with a slight variation. Again, in some embodiments, system 800 will be provided with two adapters 802, two removable reservoirs 810 and one hand-expression funnel 816, but alternatively any combination and number of those three components may be provided. FIG. 11A illustrates adapter 802 by itself (left panel), reservoir 810 by itself (middle panel), and the two components coupled together (right panel). The only difference in the embodiment of system 800 illustrated in FIGS. 11A-11D, as compared to the embodiment of FIGS. 7-10D, is that the components of system 800 do not include threads for fitting together but instead simply slide or press onto one another.

Figure 11B:
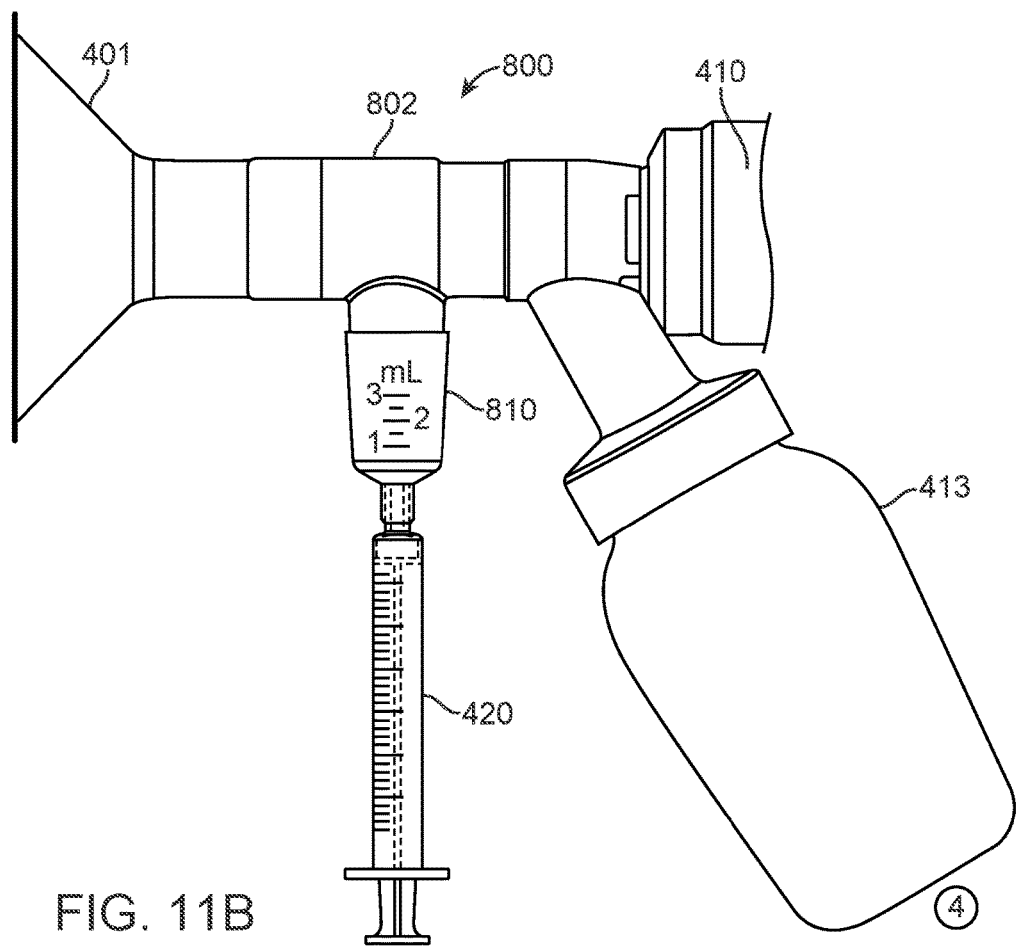
FIG. 11B is a side view of the adapter and removable reservoir of FIG. 11A, attached to a breast pump system.
Figure 11D:
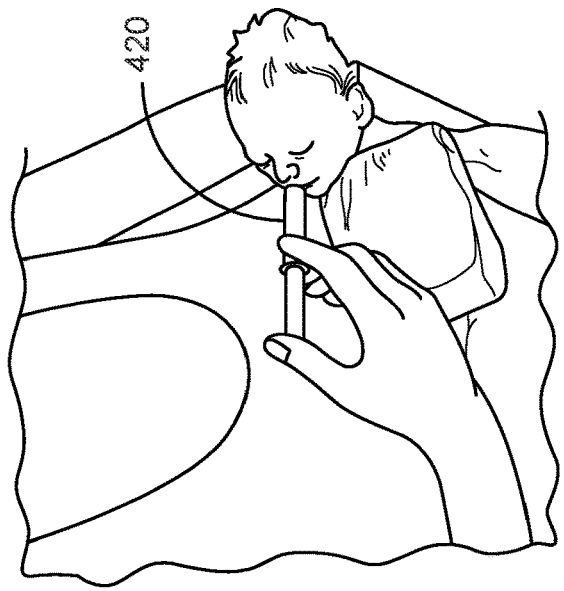
FIG. 11D is a perspective view of a woman feeding a newborn colostrum, using the syringe of FIG. 11C.
Figure 11C:
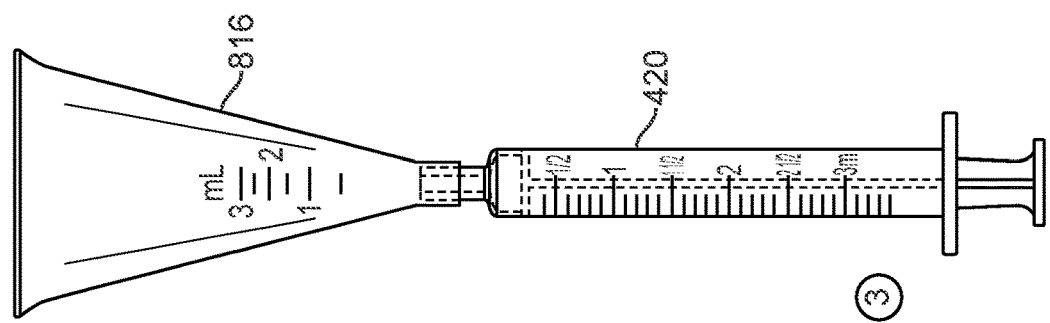
FIG. 11C is a side view of a hand-expression funnel and a syringe of a colostrum collection system, according to one embodiment.
Figure 11C:
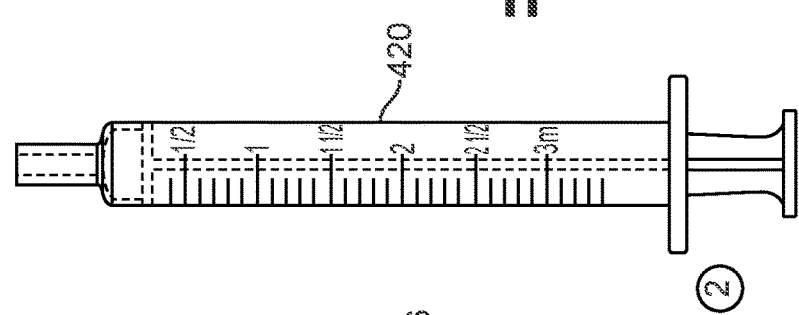
Figure 11C:
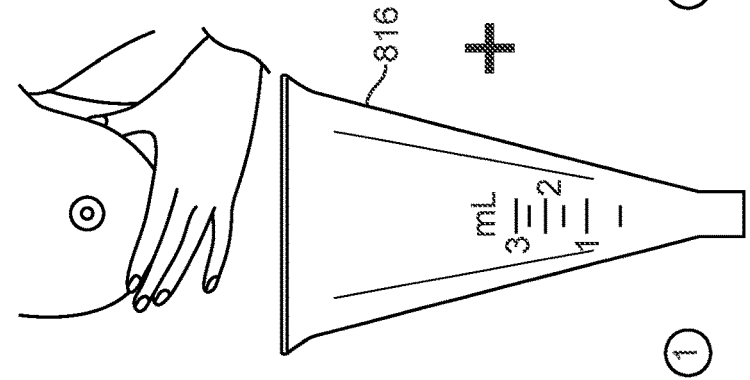

FIG. 11B shows colostrum collection and delivery system 800 coupled with a breast pump shield 401 and connector 410, as well as with syringe 420 and a milk bottle 413. FIG. 11C illustrates funnel 816 by itself (left panel), syringe 420 by itself (middle panel) and the two components coupled together (right panel). In use, the woman attaches funnel 816 to syringe 420, hand expresses colostrum into funnel 816, pulls the colostrum into syringe 420 by pulling back the plunger of syringe 420, and detaches syringe 420 from funnel 416. As illustrated in FIG. 11D, the narrow end of syringe 420 may then be placed in the newborn's mouth for delivery of the colostrum. As mentioned above, in any given embodiment, colostrum collection and delivery system 800 may be used by a nursing woman in any suitable manner, for example any combination of breast pumping and hand expressing, or only one of the two methods.

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Modifications and variations are intended to be included within the scope of the application.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications without departing from the scope of the present invention. For instance, the examples, embodiments, geometrics, materials, dimensions, ratios, steps, and the like discussed above are illustrative and are not required. Accordingly, the scope of the present invention is not limited to the details of structure and operation shown and described in the specification and drawings.

What is claimed is:

1. An adapter system for facilitating collection of colostrum from a breast, the adapter system comprising:
   an adapter, comprising:
      a body having a funnel connecting end for connecting to a breast shield of a breast pump system and a breast pump connecting end for connecting to a breast pump connector of the breast pump system;
      a side port comprising a dispensing end, disposed between the funnel connecting end and the breast pump connecting end, configured for allowing the colostrum to pass out of the adapter;

a block inside the body, between the breast pump connecting end and the dispensing end, for directing the colostrum through the dispensing end, wherein the block comprises a flat wall oriented perpendicular to a cylindrical wall that forms the body of the adapter; and an aperture in the block to allow suction force applied at the breast pump connecting end to generate suction at the funnel connecting end;

a removable reservoir comprising a wide end for removably attaching to the dispensing end of the adapter and a narrow end for attaching to a colostrum delivery device; and a hand-expression funnel comprising a wide end for receiving colostrum and a narrow end for attaching to the colostrum delivery device.

2. The adapter system as in claim 1, wherein the aperture comprises a circular hole through the block.

3. The adapter system as in claim 2, wherein the circular hole is located closer to a top of the body of the adapter than to a bottom of the body of the adapter.

4. The adapter system of claim 1, wherein the funnel connecting end has a first inner diameter that is larger than a second inner diameter of the breast pump connecting end.

5. The adapter system of claim 1, wherein the removable reservoir and the hand-expression funnel each comprise fluid level markings for measuring an amount of the colostrum.

6. The adapter system of claim 1, wherein the colostrum delivery device comprises a syringe.

7. The adapter system of claim 6, wherein the narrow end of the removable reservoir comprises threads on its inner surface for coupling with outer threads on the syringe.

8. The adapter system of claim 7, wherein the wide end of the removable reservoir comprises threads on its inner surface for coupling with outer threads on the dispensing end of the adapter.

9. The adapter system of claim 6, wherein the narrow end of the hand-expression funnel comprises threads on its inner surface for coupling with outer threads on the syringe.

10. The adapter system of claim 1, further comprising:
at least one additional adapter; and
at least one additional removable reservoir.

* * * * *